US00PP24134P2

(12) United States Plant Patent
Van Der Kolk

(10) Patent No.: US PP24,134 P2
(45) Date of Patent: Dec. 31, 2013

(54) ***COREOPSIS* PLANT NAMED 'TAHITIAN SUNSET'**

(50) Latin Name: *Coreopsis rosea*
Varietal Denomination: Tahitian Sunset

(76) Inventor: Peter Van Der Kolk, Hudsonville, MI (US)

( * ) Notice: Subject to any disclaimer, the term of this patent is extended or adjusted under 35 U.S.C. 154(b) by 99 days.

(21) Appl. No.: 13/385,336

(22) Filed: Feb. 14, 2012

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Susan McCormick Ewoldt

(57) ABSTRACT

The new and distinct cultivar of ornamental Tickseed, *Coreopsis* 'Tahitian Sunset' with short, compact, intensely-floriferous, long-blooming habit and flowers with a blend of watermelon-red and golden-orange petals. It is grown as an annual in zones colder than USDA zone 8 and as a perennial in zones 8 through 10.

1 Drawing Sheet

Botanical classification: *Coreopsis rosea.*
Variety denomination: 'Tahitian Sunset'.

BACKGROUND OF THE INVENTION

The present invention relates to a new and distinct cultivar of ornamental Tickseed plant, botanically of hybrid origin and known as *Coreopsis* 'Tahitian Sunset' and will be referred to hereinafter by its cultivar name, 'Tahitian Sunset', the new plant or new cultivar. The new cultivar of *Coreopsis* was discovered in August 2009 by Peter Van Der Kolk as a whole plant mutation of *Coreopsis* 'Sweet Dreams' U.S. Plant Pat. No. 12,720 at a nursery in Hudsonville, Mich., USA. *Coreopsis* 'Tahitian Sunset' was first propagated by vegetative tip cuttings at the same nursery in Hudsonville, Mich. in August 2009. The resultant plants and those of successive generations of asexual propagation have been evaluated to be true to the original plant and stable.

SUMMARY OF THE INVENTION

The new plant *Coreopsis* 'Tahitian Sunset' can be most closely compared to its parent sport 'Sweet Dreams' and another sport of 'Sweet Dreams', *Coreopsis* 'Heaven's Gate' U.S. Plant Pat. No. 16,016. Both of the above plants are selections from *Coreopsis rosea*. Habit and foliage of all three above plants is similar to indistinguishable. In comparison, both 'Heaven's Gate' and 'Sweet Dreams' have ray florets with deep purplish basal coloring of the eye of the ray florets while the distal regions of the ray florets of the two comparison plants are light violet and white respectively while the 'Tahitian Sunset' has watermelon-red on the outer portion of the ray petals and golden orange on the center eye of the ray petals. The following traits have been repeatedly observed and are determined to be the unique and stable characteristics of the new cultivar:

1. Short, compact, well-branched habit.
2. Fine linear foliage.
3. Intensely-floriferous and long-blooming.
4. Flowers with ray petals having watermelon-red on the outside and blending to golden-orange on the inside.

*Coreopsis* 'Tahitian Sunset' can also be compared to other plants with *Coreopsis rosea* or hybrids of *Coreopsis rosea*. *Coreopsis* 'Limerock Ruby' U.S. Plant Pat. No. 15,455 has a solid ruby red flower. *Coreopsis* 'Autumn Blush' U.S. Plant Pat. No. 18,184, 'Snowberry' U.S. Plant Pat. No. 18,560 and *Coreopsis* 'Coreopram' U.S. Plant Pat. No. 19,932 are all two-tone with creamy yellow petal margins and maroon centers and 'Coreopram' has tri-lobed foliage. The related group of *Coreopsis* 'Caliente' U.S. Plant Pat. No. 21,869, *Coreopsis* 'Jive' U.S. Plant Pat. No. 22,015, *Coreopsis* 'Salsa' U.S. Plant Pat. No. 22,129 and *Coreopsis* 'Mambo' U.S. Plant Pat. No. 22,131 all have maroon petal centers and yellow, pink, creamy white to red petal perimeters, and *Coreopsis* 'Limbo' U.S. Plant Pat. No. 22,130 is all white with nearly white petal centers.

BRIEF DESCRIPTION OF THE DRAWING

The photographs of the new invention demonstrate the overall appearance including the unique traits of the new plant. Light source direction may cause the appearance of variation in color. The colors are as accurate as reasonably possible with color reproductions. The plants used for this photograph were one year old and near the end of the summer grown in an open sun trial garden in Zeeland, Mich.

DETAILED BOTANICAL DESCRIPTION

Figure 1:
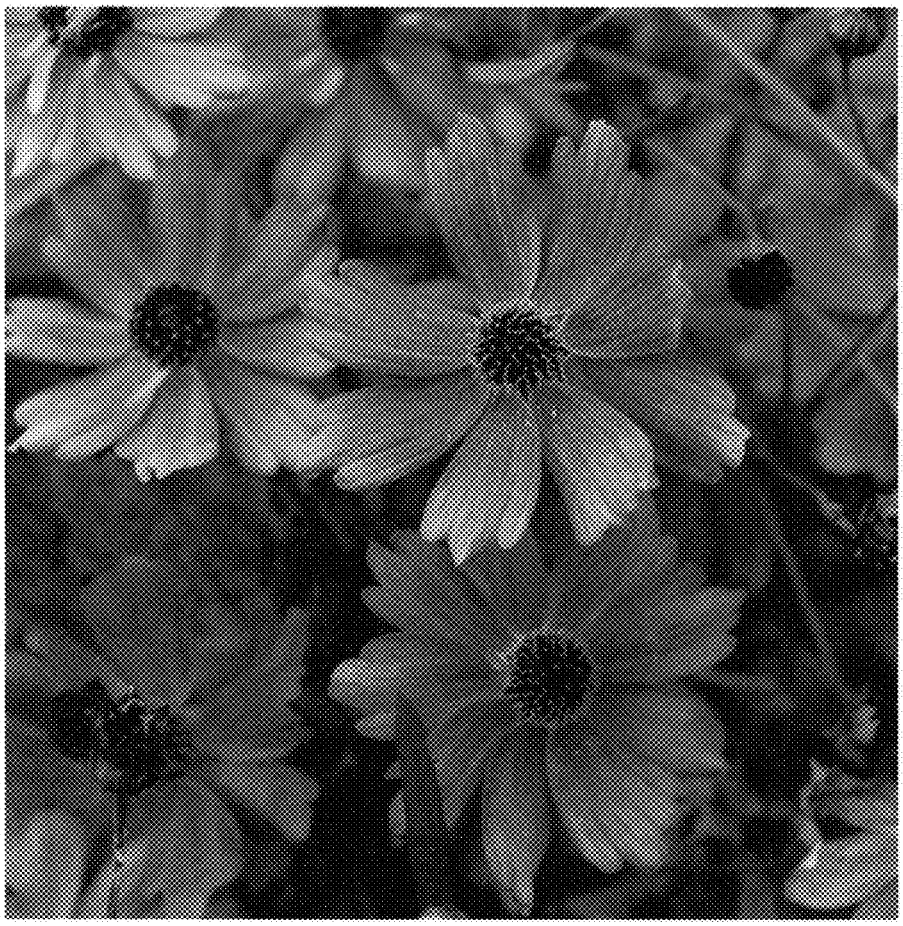
FIG. 1 shows a close-up of the flowers of 'Tahitian Sunset' with the watermelon-red petals going toward yellow in the center.
Figure 2:
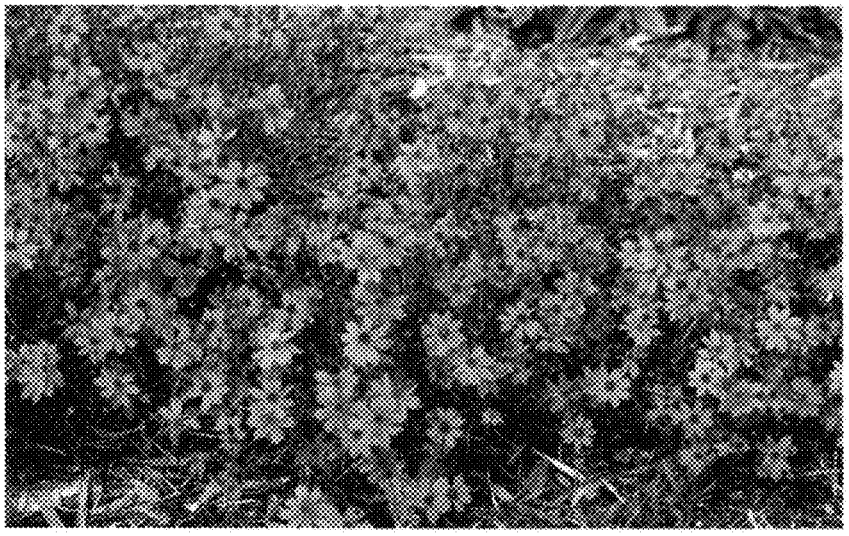
FIG. 2 shows a mature plant of 'Tahitian Sunset' in the landscape.

The following color descriptions are based on color terminology in accordance with The Royal Horticultural Society "Colour Chart" 2001 edition and are labeled with R.H.S. and the appropriate corresponding reference number and letter except where common dictionary terms are used. The plant described is a single-season, seven-month old plant grown in a trial garden in Zeeland, Mich. with supplemental fertilizer and water when necessary but without plant growth regulators. *Coreopsis* 'Tahitian Sunset' has not been tested in all possible environmental conditions and may appear phenotypically different under different conditions without any difference in genotype.

Parentage: Whole plant mutation of *Coreopsis* 'Sweet Dreams'.

Plant habit: Tender herbaceous perennial then spread and arch later in season.

Plant size: To about 35 cm tall and 48 cm diameter; spreading more than height in maturity.

Plant vigor and growth rate: Rapid, rooting from tip cuttings in 10 to 14 days, finishing in a 2.5 cm plug in five weeks and from a 2.5 cm plug to a one liter container in about six weeks.

Root description: Fine, fibrous, and well-branched.

Stem: Nearly round, glabrous, lustrous; 1.0 to 2.0 mm diameter; branching with usually two axillary branches at each lower node; internode length between 1.5 and 2.5 cm; stem strength is moderate and flexible; total main stem length about 30 cm; secondary and tertiary stems between 20 cm and 4 cm long.

Stem color: Between RHS 143A and RHS 137D.

Foliage: Simple, entire, rarely one to two lateral lobed, opposite, linear with acute apex and attenuate base, sessile slightly lucid both surfaces; size variable, up to 3.5 cm long and 3.0 mm wide; held horizontal to upright at 45 degrees from horizontal.

Leaf color: Adaxial nearest RHS 137C; abaxial nearest RHS 138A.

Venation: Pinnate, not prominent, vein color same as leaf color; Inflorescence buds about three days prior to anthesis: spherical, about 8.0 mm diameter; color made up of a mixture of RHS 187A and RHS 183A mostly near top with RHS N172B and RHS N163C along the sides of the bud.

Flowering timing: Beginning late spring and lasting into fall, for over 15 weeks.

Flower: Composite with usually eight ray florets surrounding about 55 disk florets in the center forming a domed radiant head; size about 4.5 cm diameter and 5.0 mm height, receptacle about 4.0 mm diameter; about 100 flowers per plant at a time during peak season.

Ray florets: Eight in number, sterile; ray petals held perpendicular to peduncle, or to produce a flat flower face; petals oblong, apex emarginate to three-lobed, cleft about 1.0 mm deep, with largest lobe in center about 3.5 mm long and 3.5 mm wide, base attenuate and bent in a near 90 degree angle.

Petal color: Adaxial side: nearest RHS 39A on the distal portion and gradually becoming more yellow to nearest RHS 21B at the base; abaxial side: nearest RHS 39C on distal portion and blending toward RHS 29A at base.

Disk florets: About 55 in number, perfect, petalostemonous, petals apex acute, base fused into corolla; petal length about 3.0 mm long, corolla about 1.0 mm diameter; color nearest RHS 183B.

Gynoecium: One per disk floret.

*Style.*—Fine, about 3.5 mm long and less than 0.5 mm diameter; color nearest 160A, translucent.

*Stigma.*—Bifid in last 1.5 mm, less than 0.5 mm diameter and curled around nearly 360 degrees; color between RHS 21C and RHS 22C.

*Ovary.*—Inferior; about 1.0 mm long and 0.5 mm in diameter; color nearest RHS 145D.

Androecium: Five, petalostemonous.

*Stamen.*—Five, finely filamentous, about 2.0 mm long and 0.2 mm diameter; color nearest.

*Anther.*—Oblong, about 1.5 mm long and 0.3 mm diameter; color nearest RHS.

*Pollen.*—Spherical, abundant, less than 0.1 mm in diameter, color nearest RHS 8C.

Lastingness: About seven days; petals self-cleaning, bracts and disk flowers persistent.

Fragrance: None detected.

Phyllaries: In two rows; distal row of eight, deltate-ovate, entire, glabrous, acute apex and sessile truncate base, about 4.0 mm long and 2.0 mm wide at base; proximal row of five, linear, entire, glabrous, acute apex and attenuate base, about 2.0 mm long and 0.5 mm wide.

Phyllary color: Distal set adaxial color nearest RHS 137A with margins less than 0.5 mm width of RHS 24A; distal abaxial color nearest RHS 137A with margins less than 0.5 mm width of RHS 24B; proximal set adaxial color nearest RHS 137B with a margin of less than 0.3 mm of nearest RHS 138D; proximal set abaxial colors the same as adaxial.

Peduncle: Nearly round, glabrous, lustrous; strong, wiry; up to 4.5 cm long, average about 2.5 cm long and 1.0 mm diameter; color nearest RHS 137B.

Fruit and seed: Has not yet been observed.

Resistance: Resistance to diseases and pests beyond that typical to *Coreopsis* has not been noted; 'Tahitian Sunset' has shown tenderness in USDA zone 6 but is hardy in zones 8 to 10.

It is claimed:

1. The new and distinct *Coreopsis* plant named 'Tahitian Sunset' as herein described and illustrated, useful as a potted plant, landscape plant, cut flower, and to attract butterflies.

* * * * *